United States Patent
Wang et al.

(10) Patent No.: US 11,235,082 B2
(45) Date of Patent: Feb. 1, 2022

(54) HUMIDIFIER WITH DISINFECTION UNIT

(71) Applicant: KONINKLIJKE PHILIPS N.V., Eindhoven (NL)

(72) Inventors: Bao Wang, Nanjing (CN); Michael Martin Scheja, Shanghai (CN); John Robert McGarva, Newton Stewart (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/754,212

(22) PCT Filed: Oct. 4, 2018

(86) PCT No.: PCT/EP2018/076947
§ 371 (c)(1),
(2) Date: Apr. 7, 2020

(87) PCT Pub. No.: WO2019/072668
PCT Pub. Date: Apr. 18, 2019

(65) Prior Publication Data
US 2021/0187150 A1    Jun. 24, 2021

(30) Foreign Application Priority Data
Oct. 13, 2017 (WO) ................ PCT/CN2017/106002
May 29, 2018 (EP) ..................................... 18174776

(51) Int. Cl.
*A61L 9/20* (2006.01)
*F24F 3/14* (2006.01)
(Continued)

(52) U.S. Cl.
CPC ........ *A61L 9/20* (2013.01); *B01F 3/04* (2013.01); *F24F 3/14* (2013.01); *F24F 6/16* (2013.01);
(Continued)

(58) Field of Classification Search
CPC ....... F24F 3/14; F24F 8/22; A61L 9/20; B01F 3/04
See application file for complete search history.

(56) References Cited

U.S. PATENT DOCUMENTS 3,705,479 A * 12/1972 McPherson .......... B01D 47/028
96/259
8,940,085 B2 * 1/2015 Markham ................. F24F 3/16
96/224
(Continued)

FOREIGN PATENT DOCUMENTS

CN    104395676 A    3/2015
CN    104676768 A    6/2015
(Continued)

OTHER PUBLICATIONS

International Search Report and Written Opinion dated December 13, 2018 for International Application No. PCT/EP2018/076947 Filed October 4, 2018.
(Continued)

*Primary Examiner* — Robert A Hopkins
(74) *Attorney, Agent, or Firm* — Schott, P.C.

(57) ABSTRACT

Presented is a humidifier, comprising: a rotatable wick; a means for rotating the wick; characterized in that: the humidifier further comprises a disinfection unit adapted such that different parts of the wick are disinfected when the wick rotates.

15 Claims, 6 Drawing Sheets

(51) Int. Cl.
*F24F 8/22* (2021.01)
*B01F 3/04* (2006.01)
*F24F 6/16* (2006.01)
*F24F 6/00* (2006.01)

(52) U.S. Cl.
CPC ............ *F24F 8/22* (2021.01); *A61L 2202/11* (2013.01); *F24F 2006/008* (2013.01)

(56) References Cited

U.S. PATENT DOCUMENTS

| | | |
|---|---|---|
| 2002/0190400 A1 | 12/2002 | Bachert |
| 2015/0090121 A1 | 4/2015 | Markham |

FOREIGN PATENT DOCUMENTS

| | | |
|---|---|---|
| CN | 204388277 U | 6/2015 |
| CN | 106958882 A | 7/2017 |
| EP | 1600702 | 7/2016 |
| GB | 2140912 | 12/1984 |
| KR | 20170011634 | 2/2017 |
| KR | 20170090209 | 8/2017 |
| WO | 2016/052885 | 4/2016 |

OTHER PUBLICATIONS

Amirdivani, et al: "A Heated Water Humidifier with a Rotating Wick" Anesth Analg, 55,244-246, 1979.

* cited by examiner

HUMIDIFIER WITH DISINFECTION UNIT

CROSS REFERENCE TO RELATED APPLICATIONS

This application is the U.S. National Phase application under 35 U.S.C. § 371 of International Application No. PCT/EP2018/076947 filed Oct. 4, 2018, published as WO 2019/072668 on Apr. 18, 2019, which claims the benefit of European Patent Application Number 18174776.7 filed May 29, 2018 and Application Number PCT/CN2017/106002 filed Oct. 13, 2017. These applications are hereby incorporated by reference herein.

FIELD OF THE INVENTION

The present invention relates to humidifiers. In particular, the invention relates to humidifiers with disinfection capabilities.

BACKGROUND OF THE INVENTION

Humidifiers are available from many brands and are widely used to increase the humidity level of air in indoor spaces. Different architectures have been developed based on different principles. These humidifiers share a common feature, namely, a water tank which is a reservoir for the water used for humidifying the air.

A problem related to water being present in the water tank is the growth of microorganisms. This is disturbing to the user as over time it creates an unpleasant smell. Further, this may also lead to health issues for the user, for example when microorganisms and/or their by-products such as Microbial Volatile Organic Compounds (MVOCs) are released into the air. The growth of microorganisms also occurs inside the wick which absorbs water from the water tank and which is used to evaporate water from.

US 2015/0090121A1 discloses a humidifier with ultraviolet disinfection. A system and a method for humidifying air is disclosed. The system includes an atomizer and an ultraviolet light source. The atomizer increases the moisture content of a volume of air, and the ultraviolet light sources exposes the resulting humidified air with germicidal light prior to dispersal of the humidified air into the ambient environment.

There is a need for a humidifier in which the growth of microorganisms in the wick and/or in the water tank can be effectively reduced. Ideally, the water tank and the wick should be disinfected at the same time.

SUMMARY OF THE INVENTION

In an aspect of the invention, a humidifier is presented, comprising: a rotatable wick; a means for rotating the wick; wherein the humidifier further comprises a disinfection unit adapted such that different parts of the wick are disinfected when the wick rotates. For example, the disinfection unit is located, e.g. fixedly located, such that different parts of the wick are disinfected during rotation of the wick and when the disinfection unit is active. As an advantage, as the wick rotates and passes the disinfection unit, the size of the disinfection unit, e.g. the number of light sources in the disinfection unit, can be reduced while still being able to disinfect large and different parts of the wick. This increases compactness and reduces the cost of the device.

According to embodiments, the humidifier further comprises a water tank. The wick is located at least partly in the water tank; and the disinfection unit is further adapted or positioned for disinfecting content of the water tank. As the wick rotates, the water in the water tank will also rotate inside the water tank and pass by the disinfection unit such that the water is disinfected also. It is an advantage that a single disinfection unit can be used to disinfect the wick and the water in the tank. This increases compactness and reduces cost of the humidifier.

According to embodiments, a first element of the disinfection unit is located near an outer surface of the water tank such that the wick, the water tank and content of the water tank are disinfected when the humidifier is activated.

According to embodiments, the water tank is hollow-cylindrically shaped, a second element of the disinfection unit is located near an outer surface of the water tank inside the hollow part of the water tank such that the wick, the water tank and content of the water tank are disinfected when activated. It is an advantage of the invention that by using a hollow-cylindrically shaped water tank, a part of the disinfection unit can be positioned inside the hollow part of the water tank. This further increases compactness, reduces cost but more importantly allows disinfection of the wick from a different location relative to the location of the first element. This increases the disinfection effectivity of the system.

According to embodiments, the means for rotating the wick is motor-less and configured for rotating the wick when an air flow is generated in the humidifier. According to embodiments, the means for rotating the wick is located in an air flow path inside the humidifier; and the means for rotating the wick is configured for converting a force exerted by an air flow in the air flow path on the means for rotating the wick into a rotational force for rotating the wick. It is an advantage of the invention that manufacturing costs and total cost of the device can be reduced by removing the need of a motor for rotating the wick. A further advantage is that the lack of such a motor allows the humidifier to be more compact, lighter and portable.

According to embodiments, the means for rotating the wick comprises wind blades coupled to the wick such that the wick rotates when the wind blades rotate.

According to embodiments, the wick is hollow-cylindrically shaped and at least a part of the means for rotating the wick is located inside the hollow part of the wick. It is an advantage that the compactness of the humidifier can be increased by placing the means for rotating the wick in the hollow part of the wick.

According to a particular embodiment, the means for rotating the wick may comprise a motor.

According to embodiments, the wick is designed to partially float in water when immersed. For example, the wick material is selected to partially float in water when immersed. For example, the wick may comprise a floating material which allows the wick to float when immersed in water. This eases the rotation of the wick inside the water tank.

According to embodiments, the disinfection unit comprises a light source. The light source is located upstream of the wick such that air propagating through the humidifier is heated before passing through the wick. As an advantage, the temperature of the air inside the humidifier increases while the relative humidity of the air inside the humidifier decreases before reaching the wick. This results in a more effective water uptake when the air propagates through the wick and thus in a more efficient humidification performance.

According to embodiments, the light source is coupled to a heat sink. This allows a better cooling of the light source and a better heating of the air before passing through the wick.

According to a particular embodiment, the disinfection unit comprises a light source and the light source is coupled to a heat sink that is located upstream of the wick such that air propagating through the humidifier is heated before passing through the wick.

According to embodiments, the disinfection unit comprises an array of light emitting diodes (LEDs).

According to embodiments, the humidifier comprises an air pollutant filter located upstream of the wick. As an advantage, the wick is not contaminated with pollutants.

According to embodiments, the disinfection unit comprises electromagnetic radiation sources comprising one or more of the following sources: UVA, UCB or UVC, 405 nm light source, or IR.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 6 illustrates a 3D view of an embodiment of the humidifier The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In an aspect of the invention, a humidifier is presented. The humidifier comprises: a rotatable wick; a means for rotating the wick; and a disinfection unit. The disinfection unit is located inside the humidifier such that different parts of the wick are disinfected during rotation of the wick.

By exposing the wick of the humidifier to a disinfection unit, the growth of micro-organisms such as bacterium, virus, or fungus is reduced. The disinfection unit may comprise radiation sources, e.g. electromagnetic radiation sources such as UVA, UVB or UVC, 405 nm, or IR. The humidifier is constructed such that the wick can rotate inside the humidifier, e.g. inside a water tank of the humidifier. One or more radiation sources are present inside the humidifier and are located such the wick can be disinfected by the produced radiation of the radiation source(s). As the wick rotates inside the humidifier, the wick and the disinfection unit are positioned such that different parts of the wick are exposed to the disinfection unit, e.g. exposed to radiation of the disinfection unit. For example, the disinfection unit is fixedly located inside the humidifier and as the wick rotates, different parts of the wick are exposed to the radiation of the disinfection unit.

It is an advantage of the invention that by rotating the wick, the number of disinfection units, e.g. the number of radiation sources, can be reduced while still being able to effectively disinfect different parts of the wick. In other words, because the wick is rotating and different parts of the wick are passing the disinfection unit, there is no need to have several disinfection units to disinfect different parts of the wick. This means that, for example, one disinfection unit may be fixedly located inside the humidifier and capable of disinfecting the complete wick as the wick rotates, depending on how deep the radiation of the disinfection unit is capable of penetrating and thus disinfecting the wick.

According to an embodiment of the invention, the humidifier, further comprises a water tank. The wick is located at least partly in the water tank. The disinfection unit is further positioned for disinfecting content present in the water tank. It is an advantage of the invention that the disinfection unit also disinfects the content of the water tank. As the wick rotates inside the water tank, liquid content in the water tank will also rotate inside the water tank through the force of the wick. The disinfection unit may be sized such that the part of the wick located in the water tank and the part of the wick located outside of the water tank can be disinfected.

According to an embodiment, the disinfection unit is located inside the water tank. As an advantage, the disinfection unit may be located closer to the wick, leading to a more effective disinfection of the wick and water in the water tank. In such an embodiment, the disinfection unit may be waterproof.

According to an embodiment, the disinfection unit is located outside of the water tank. In such an embodiment, the material of the water tank is selected to allow penetration of radiation from the disinfection unit and thereby allow disinfection of the water tank content and the wick. For example, the water tank is made from a transparent material. In a particular embodiment, the disinfection unit comprises a first element which is located near an outer surface of the water tank such that the wick, the water tank and content of the water tank are disinfected when activated. Optionally, the water tank is hollow-cylindrically shaped and the disinfection unit comprises a second element. This second element is located near an outer surface of the water tank and inside the hollow part of the water tank such that the wick, the water tank and content of the water tank are disinfected when activated. The second element may also be located at a location near the wick, different from the first element. It should be noted that the disinfection unit may comprise a plurality of disinfection elements. However, it may also consist of a single disinfection element which may comprise different radiation components such as light sources.

According to an embodiment, the means for rotating the wick is motor-less and configured for rotating the wick when an air flow is generated in the humidifier. In a particular embodiment, the means for rotating the wick is located in an air flow path inside the humidifier and the means for rotating the wick is configured for converting a force exerted by an air flow in the air flow path on the means for rotating the wick into a rotational force suitable for rotating the wick. For example, a fan may be present in the humidifier, for generating an air flow inside the humidifier. Before the air flow propagates through the wick for humidifying the air flow, the air flow hits the means for rotating the wick. When the air flow reaches the means for rotating the wick, when the force of the air flow is strong enough, the means for rotating the wick starts to rotate. As the means for rotating the wick is coupled to the wick, the wick starts to rotate as well. The means rotating the wick may comprise wind blades coupled or attached to the wick. This allows the wick to rotate when the wind blades rotate. It is an advantage of the invention that a separate motor is not required to drive the wick. This reduces cost, size and weight of the humidifier.

In an alternative embodiment, the means for rotating the wick comprises a motor. Ideally the motor is not located in an air flow generated inside the humidifier. Alternatively, the motor comprises an aerodynamic shield adapted to minimize air resistance and disturbance of the air flow.

According to an embodiment, the wick is hollow-cylindrically shaped, e.g. donut-shaped, and at least a part of the means for rotating the wick is located inside the hollow part of the wick. In such an embodiment, the water tank comprises a hollow part. When the wick is inside the water tank, the means for rotating the wick is located inside the hollow part of the water tank. As the wick rotates inside the humidifier, the hollow-cylindrical shape of the wick allows the purifier to be very compact. Also, the hollow-cylindrical shape of the wick allows the means for rotating the wick to be located inside the wick which further increases compactness of the humidifier. To further increase compactness of the humidifier, the water tank is also hollow-cylindrically shaped and dimensioned to fit the hollow-cylindrically shaped wick such that the wick may rotate inside the water tank without experiencing or minimizing friction between inner walls of the water tank and outer surfaces of the wick.

According to an embodiment of the invention, the wick material is selected to partially float in water when immersed. When water is sufficiently present in the water tank, the wick material is partially located in water. This allows the absorbing of water by the wick. The part of the wick that is not located in water is located in an air flow generated in the humidifier. This air flow propagates through the wick and exits the humidifier at the top of the humidifier.

According to an embodiment, the disinfection unit comprises a light source. In this embodiment, the light source is located upstream of the wick such that air propagating through the humidifier is heated with heat generated by the light source before passing through the wick. Thus, in such an embodiment the light source has a double functionality. The light source is adapted to disinfect the wick and/or the water tank and its content. The light source is used to heat up the air before the air is humidified by the wick material as it passes through the wick. The light source may be located in or near the air flow generated inside the humidifier, this ensures that the light source is sufficiently cooled and increases the life-time of the light source. For this purpose, the light source may be coupled to a heat sink which further increases cooling of the light source. Further, as the light source dissipates heat, the temperature of the air inside the humidifier increases while its relative humidity decreases before reaching the wick. This results in a more effective water uptake. This means that higher airflows can be realized to reach the same absolute water concentration in the air leaving the wick, which ultimately leads to higher humidification rates which is the key performance parameter of a humidifier.

According to an embodiment, the humidifier further comprises an air pollutant filter located upstream of the wick. For example, this filter may be located upstream or downstream of a fan used to generate an air flow in the humidifier. The filter may be located at the bottom of the humidifier. The filter may be located at the air inlet of the humidifier. The filter may be a cylindrical air pollutant removal structure such as a HEPA filter, gas filter, combi-filter, ESP unit, catalyst. As an advantage, the air flow reaching the means for rotating the wick, the wick and the resulting humidified air is free from pollutants. Thus, the humidifier may also function as an air purifier.

According to an embodiment, the disinfection unit comprises electromagnetic radiation sources comprising one or more of the following sources: UVA, UCB or UVC, 405 nm, or IR.

Figure 1:
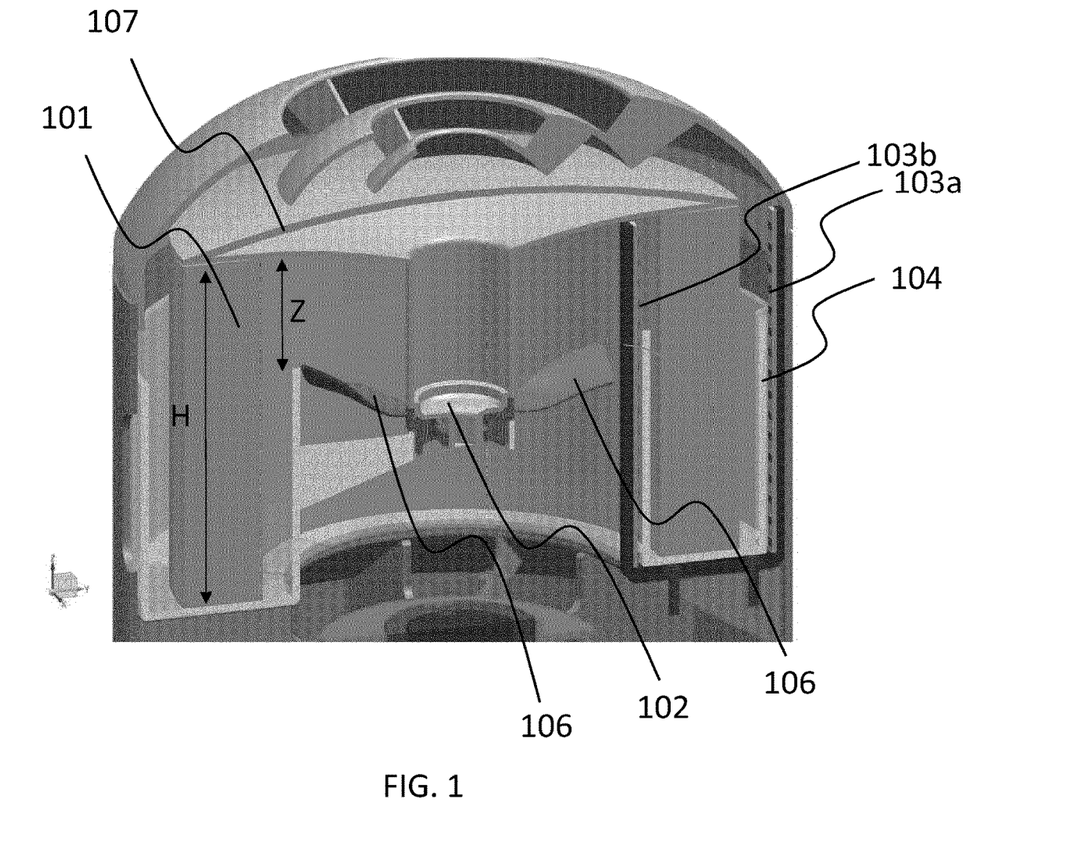
FIG. 1 illustrates a 3D cross section of an upper part of an embodiment of a humidifier

FIG. 1 illustrates a 3D cross section of an upper part of an embodiment of the humidifier 100. Inside the humidifier 100 a water tank 104 is present. Inside the water tank 104 a wick 101 is present. The water tank 104 is hollow cylindrically shaped. The wick 101 is also hollow cylindrically shaped. The size of the wick 101 is adapted to the size of the water tank 104 such that the wick 101 can easily rotate inside the water tank 104. The wick 101 is connected or attached to the means for rotating the wick 102 which comprises blades 106. The connection 107 between the wick 101 and the means for rotating the wick 102 may be a plastic or a metal part or another material suitable for making this connection. The means for rotating the wick 102 is located inside the hollow part of the water tank 104 and inside the hollow part of the wick 101. The hollow part of the water tank 104 is located in an air flow path of the humidifier 100. The hollow part of the water tank 104 is part of the air flow channel inside the humidifier 100. When an air flow is generated inside the humidifier 100, blades 106 of the means for rotating the wick 102 are subjected to the air flow and will consequently start to rotate. As the means for rotating the wick 102 is attached to the wick 101, the wick 101 will start to rotate inside the water tank 104. The disinfection unit contains two array of light sources 103a, 103b. In an alternative embodiment, the humidifier may also comprise one array of light sources. A first array of light sources 103a is located outside of the water tank 101 and positioned such that the outer surface of the wick 101 can be fully illuminated as the wick makes a 360 degrees rotation. In such an embodiment, the water tank is transparent to wavelengths emitted by the disinfection unit. In FIG. 1 the first array of light sources 103a is located on a support inside the humidifier for holding the water tank. Alternatively the first array 103a may be located on an inner wall of the humidifier 100. The second array of light sources 103b is located inside the hollow part of the water tank 104 and the hollow part of the wick 101. The second array of light sources 103b is located on a support for the water tank 104. A part of the wick 101 is located outside of the water tank 104, indicated with arrow "Z". When an air flow is generated, the air flow causes the means 102 for rotating the wick to rotate. While the wick 101 rotates, the air flow propagates through the part of the wick 101 sticking or located out of the water tank 104 such that the air gets humidified. The air flow also propagates through the part of the wick 101 that is located above water level in the water tank 104. The humidified air exits the humidifier 100 at the top of the humidifier 100.

Figure 2:
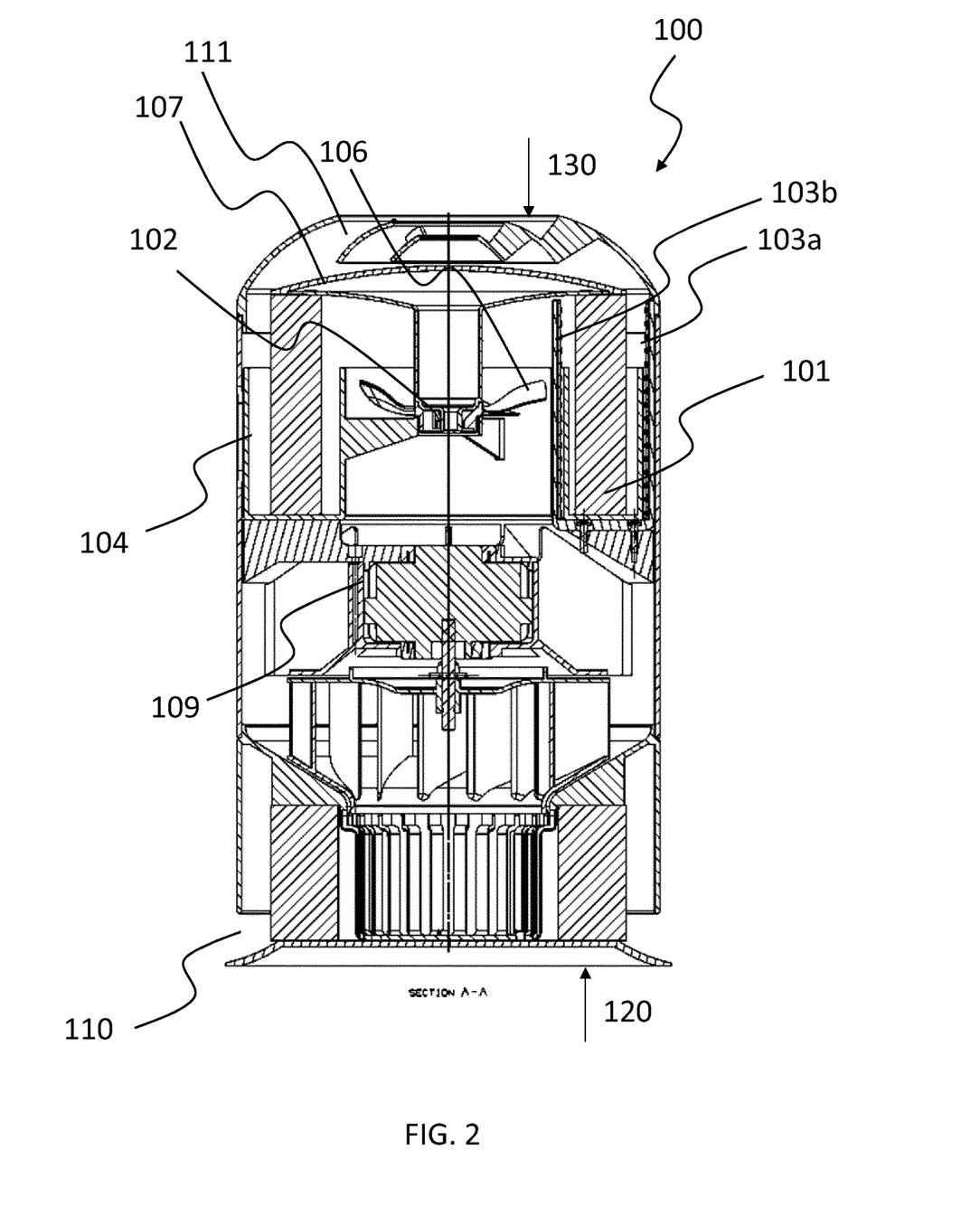
FIG. 2 illustrates a cross section of an embodiment of a humidifier

FIG. 2 illustrates a cross section of a humidifier 100. The upper part of the humidifier 100 is similar as illustrated in FIG. 1. The lower part of the humidifier 100 comprises a fan 109 for generating an air flow in the humidifier 100. The fan 109 ensures that air is sucked into the humidifier 100 via inlet 110 present at the bottom 120 of the humidifier 100, propagated through the humidifier 100 and exit the humidifier 100 at the outlet 111 present at the top 130 of the humidifier 100. The bottom 120 being defined as the part of the humidifier 100 that is used to rest on a surface in normal working mode.

Figure 3:
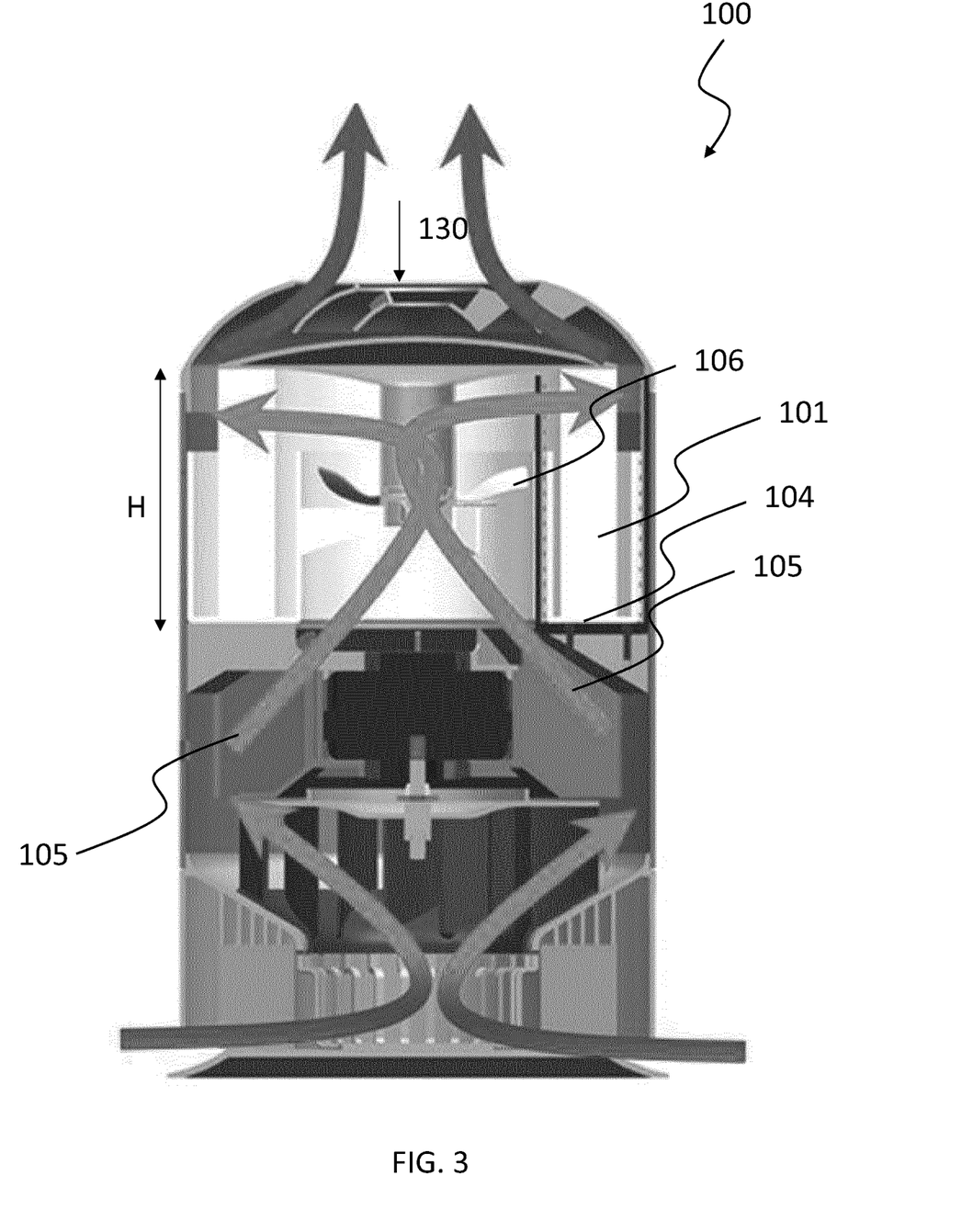
FIG. 3 illustrates a cross section of an embodiment of a humidifier whereby the arrows indicate the air flow generated inside the humidifier

FIG. 3 illustrates how the air propagates through the humidifier 100. The arrows 105 illustrate the air being sucked into the humidifier 100, the air flow hits the wind blades 106 causing the wick 101 to rotate, the air flow passes through the wick 101 as the wick 101 rotates in the water tank 104 and finally the air exits the humidifier at the top 130 of the humidifier 100. As also indicated in FIG. 1, height H of the wick 101.

According to an embodiment, the height H of the wick is larger than the height of the water tank. Thus, when the wick is located inside the water tank, a part of the wick is sticking out of the water tank. The part of the wick sticking out of the water tank is used to propagate air through and thereby humidify the air that propagates through the wick.

According to an embodiment of the invention, the disinfection unit is located on an inner wall of the humidifier. For example, the humidifier may comprise a support for holding the water tank. The disinfection unit may be located on this support for holding the water tank. As an advantage, the disinfection unit is located close to the water tank and the wick.

According to an embodiment of the invention, the means for rotating the wick may rest on a support inside the humidifier. The support is adapted to allow the mechanical structure to rotate. The support may be attached to an inner wall of the humidifier. In an embodiment this support may comprise a ball bearing. Additionally or alternatively, the support may comprise an indentation whereby the means for rotating the wick comprises a bulge or a pin suitable for resting in the indentation and whereby the means for rotating the wick is capable of rotating when resting on the support. In all embodiments, friction between the support and the means for rotating the wick should be minimal for allowing smooth rotation.

According to an embodiment, the disinfection unit comprises an array of light emitting diodes (LEDs). The shape of the array may be elongated, wherein the direction of the elongated array is perpendicular to the direction in which the wick rotates when activated. Such a construction ensures that the wick can be disinfected with the least amount of required LEDs.

Figure 4:
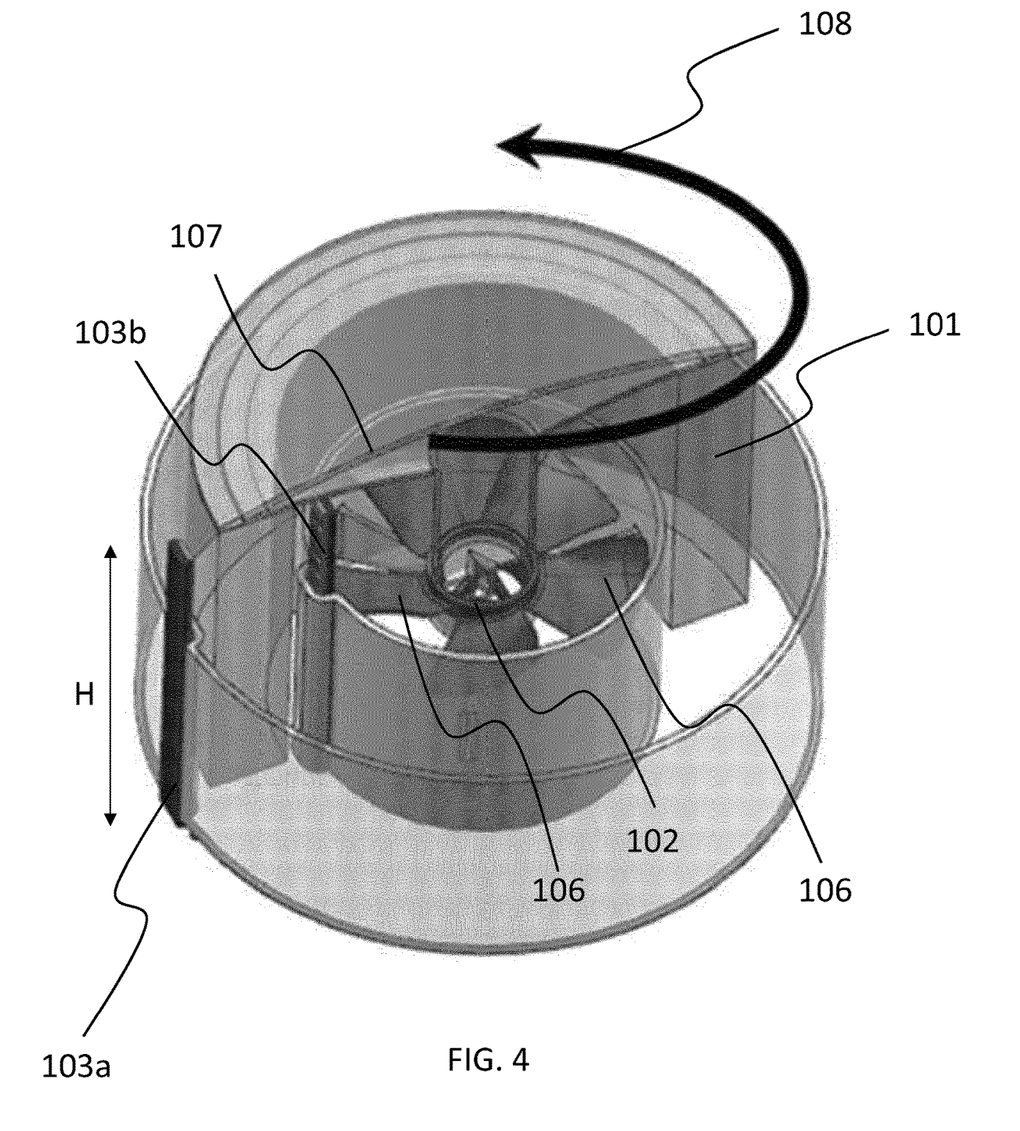
FIG. 4 illustrates the internal mechanics of an upper part of an embodiment of a humidifier, whereby the arrow indicates the rotation of the wick inside the water tank

FIG. 4 illustrates such an embodiment. Arrow 108 indicates the rotation direction of the wick 101. The wick 101 is hollow cylindrically shaped. Inside the hollow part of the wick 101 the means 102 for rotating the wick is located. The means 102 for rotating the wick comprises wind blades 106. In this embodiment, the means 102 for rotating the wick 101 is fixedly coupled to the wick 101. In embodiments, including but not limited to the embodiment depicted in FIG. 4, a mechanism may be present which minimizes the force required to rotate the wick 101, e.g. a set of gears. Array of light sources 103a, 103b are located on both sides of the wick 101. In particular, a first array of light sources 103a is located on the outside of the wick 101 and a second array of light sources 103b is located inside the wick 101, namely, inside the hollow part of the wick 101. The direction of both the first 103a and the second 103b array of light sources are perpendicular to the rotation direction 108 of the wick. Ideally, the height H (also illustrated in FIG. 1, FIG. 3 and FIG. 4) of the array of light sources 103a, 103b is adapted to the height of the wick 101 such the complete wick 101 can be illuminated and thereby disinfected.

Figure 5:
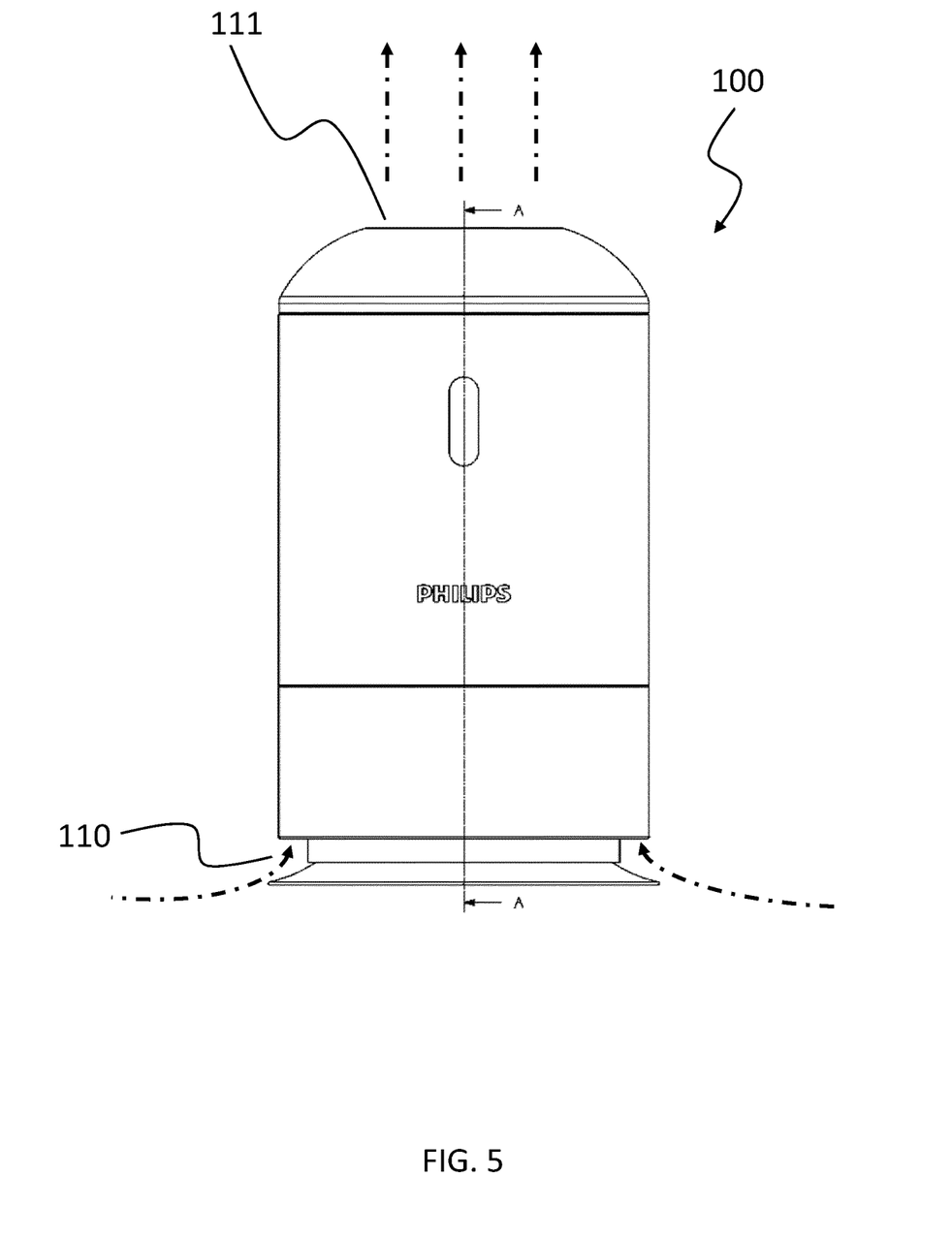
FIG. 5 illustrates a frontal view of an embodiment of the humidifier whereby arrows indicate air entering the humidifier at the bottom of the humidifier and air exiting the humidifier at the top of the humidifier

FIG. 5 illustrates a frontal view of an embodiment of a humidifier 100. The dotted-line arrows indicate the locations where air enters and exits the humidifier 100 when the fan inside the humidifier 100 is activated.

Figure 6:
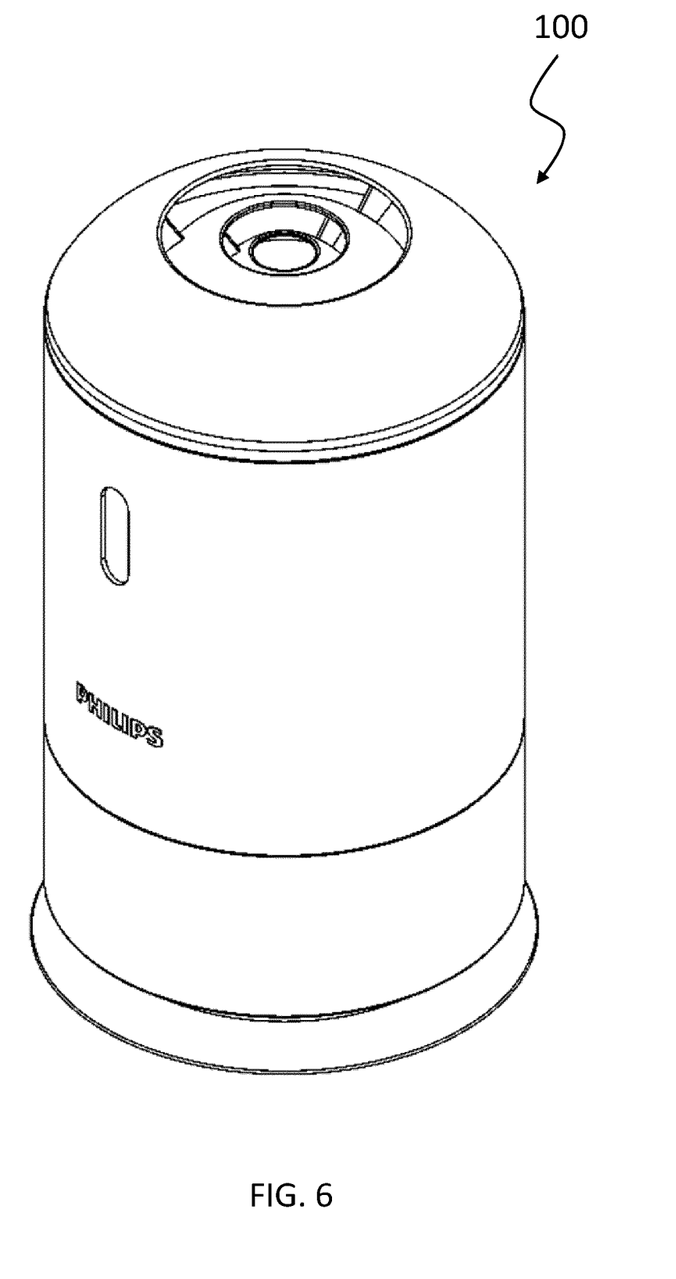

FIG. 6 illustrates a 3D line drawing of an embodiment of the humidifier 100.

The invention claimed is:

1. A humidifier, comprising:
    a rotatable wick;
    a means for rotating the wick; and
    a disinfection unit adapted such that different parts of the wick are disinfected when the wick rotates.

2. The humidifier according to claim 1, further comprising a water tank, wherein the wick is located at least partly in the water tank, and wherein the disinfection unit is positioned for disinfecting content of the water tank.

3. The humidifier according to claim 2, wherein a first element of the disinfection unit is located near an outer surface of the water tank such that the wick, the water tank, and the content of the water tank are disinfected when the humidifier is activated.

4. The humidifier according to claim 3, wherein the water tank is hollow-cylindrically shaped and wherein a second element of the disinfection unit is located near an outer surface of the water tank inside a hollow part of the water tank such that the wick, the water tank, and the content of the water tank are disinfected when the humidifier is activated.

5. The humidifier according to claim 1, wherein the means is motor-less and configured for rotating the wick when an air flow is generated in the humidifier.

6. The humidifier according to claim 1,
    wherein the means is located in an air flow path inside the humidifier; and
    wherein the means is configured for converting a force exerted by an air flow in the air flow path on the means into a rotational force for rotating the wick.

7. The humidifier according to claim 6, wherein the means comprises wind blades coupled to the wick such that the wick rotates when the wind blades rotate.

8. The humidifier according to claim 1, wherein the wick is hollow-cylindrically shaped, and wherein at least a part of the means is located inside hollow part of the wick.

9. The humidifier according to claim 1, wherein the means comprises a motor.

10. The humidifier according to claim 1, wherein the wick partially floats in water when immersed.

11. The humidifier according to claim 1, wherein the disinfection unit comprises a light source, and wherein the light source is located upstream of the wick such that air propagating through the humidifier is heated before passing through the wick.

12. The humidifier according to claim 11, wherein the light source is coupled to a heat sink.

13. The humidifier according to claim 1, wherein the disinfection unit comprises an array of light emitting diodes.

14. The humidifier according to claim 1, further comprising an air pollutant filter located upstream of the wick.

15. The humidifier according to claim 1, wherein the disinfection unit comprises electromagnetic radiation sources comprising one or more of the following sources: UVA, UCB, or UVC, 405 nm, or IR.

* * * * *